(12) United States Patent
Owusu-Adom et al.

(10) Patent No.: US 9,932,438 B2
(45) Date of Patent: Apr. 3, 2018

(54) OXIRANE-CONTAINING BISANHYDROHEXITOL DERIVATIVES AND USES THEREOF

(71) Applicant: 3M INNOVATIVE PROPERTIES COMPANY, St. Paul, MN (US)

(72) Inventors: Kwame Owusu-Adom, Stone Mountain, GA (US); Kevin M. Lewandowski, Inver Grove Heights, MN (US); Jonathan E. Janoski, Woodbury, MN (US); Michael A. Kropp, Cottage Grove, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 347 days.

(21) Appl. No.: 14/363,862

(22) PCT Filed: Dec. 7, 2012

(86) PCT No.: PCT/US2012/068393
§ 371 (c)(1),
(2) Date: Jun. 9, 2014

(87) PCT Pub. No.: WO2013/090136
PCT Pub. Date: Jun. 20, 2013

(65) Prior Publication Data
US 2014/0370298 A1    Dec. 18, 2014

Related U.S. Application Data

(60) Provisional application No. 61/576,571, filed on Dec. 16, 2011.

(51) Int. Cl.
*C08G 59/26* (2006.01)
*C08L 63/00* (2006.01)
*C08G 59/24* (2006.01)
*C07D 493/04* (2006.01)
*C08G 59/50* (2006.01)

(52) U.S. Cl.
CPC .......... *C08G 59/26* (2013.01); *C07D 493/04* (2013.01); *C08G 59/24* (2013.01); *C08G 59/5006* (2013.01); *C08G 59/5046* (2013.01); *C08L 63/00* (2013.01); *Y10T 428/31515* (2015.04)

(58) Field of Classification Search
CPC ...................................................... C08G 59/26
See application file for complete search history.

(56) References Cited

U.S. PATENT DOCUMENTS

| | | | |
|---|---|---|---|
| 2,969,377 A | 1/1961 | Phillips | |
| 3,041,300 A | 6/1962 | Morrison | |
| 3,147,236 A | 9/1964 | Port | |
| 3,225,067 A | 12/1965 | Le Maistre | |
| 3,232,901 A | 2/1966 | Holm | |
| 3,272,845 A | 9/1966 | Zech | |
| 3,537,869 A | 11/1970 | Proell | |
| 4,552,798 A | 11/1985 | Ryoke | |
| 4,769,379 A | 9/1988 | Leitold | |
| 4,778,851 A | 10/1988 | Henton | |
| 5,292,903 A | 3/1994 | Conner | |
| 5,629,380 A | 5/1997 | Baldwin | |
| 5,973,082 A | 10/1999 | Elmore | |
| 6,395,810 B1 | 5/2002 | Luitjes | |
| 6,608,167 B1 | 8/2003 | Hayes | |
| 6,632,872 B1 | 10/2003 | Pellerite | |
| 7,247,684 B2 * | 7/2007 | Lopez ................ | C08G 59/5006 428/457 |
| 7,365,148 B2 | 4/2008 | Ono | |
| 7,619,056 B2 * | 11/2009 | East ..................... | C07D 493/04 528/421 |
| 2003/0026922 A1 | 2/2003 | May | |
| 2006/0020062 A1 * | 1/2006 | Bloom ................ | C07D 303/42 524/114 |
| 2010/0117027 A1 * | 5/2010 | Hirai ..................... | C08G 65/18 252/299.61 |
| 2010/0130759 A1 | 5/2010 | Gillet | |
| 2011/0281972 A1 | 11/2011 | Beccaria | |
| 2013/0331513 A1 | 12/2013 | Beccaria | |

FOREIGN PATENT DOCUMENTS

| | | |
|---|---|---|
| GB | 586141 | 3/1947 |
| JP | 2010-090108 | 4/2010 |
| JP | 2011-213716 | 10/2011 |
| WO | WO 2000/18751 | 4/2000 |

(Continued)

OTHER PUBLICATIONS

Cawse, "Polymers from renewable sources, 1. Diamines and diisocyanates containing difurylalkane moieties," Makromol. Chem., 1984, vol. 185, pp. 697-707.

Feng, "Overview of advances in sugar-based polymers," Polymers Advanced Technologies, 2011, vol. 22, pp. 139-150.

He, "Evaluation of Furfurylamines as Curing Agents for Epoxy Resins," Journal of Polymer Science: Part A: Polymer Chemistry, Mar. 1992, vol. 30, No. 4, pp. 533-542.

Pocius, *Adhesion and Adhesives Technology: An Introduction*, 2nd Edition, Hanser Gardner Publications, Inc., Cincinnati, OH, Chapter 8, "The Chemistry and Physical Properties of Structural Adhesives", pp. 201-237, (2002).

(Continued)

*Primary Examiner* — Irina Krylova
(74) *Attorney, Agent, or Firm* — Jean A. Lown

(57) ABSTRACT

Epoxy compounds that are bisanhydrohexitol derivatives (i.e., isosorbide derivatives, isomannide derivatives, isoidide derivatives, or mixtures thereof) having two terminal oxirane groups are provided. Additionally, curable compositions that include these epoxy compounds, cured compositions prepared from the curable compositions, and articles containing the cured compositions are described. The cured compositions can be used, for example, as a structural adhesive or as a coating.

1 Claim, No Drawings

(56) References Cited

FOREIGN PATENT DOCUMENTS

| | | |
|---|---|---|
| WO | WO 2008/147473 | 12/2008 |
| WO | WO 2009/023759 | 2/2009 |
| WO | WO 2011/019557 | 2/2011 |
| WO | WO 2011/048750 | 4/2011 |
| WO | WO 2011/097443 | 8/2011 |

OTHER PUBLICATIONS

International Search Report for PCT International Application No. PCT/US2012/068393, dated Oct. 17, 2013, 3 pages.
Haworth, "Some Derivatives of Simple Carbohydrates Containing Unsaturated Substituents", Journal of the Chemical Society, 1946, pp. 488-491.

* cited by examiner

OXIRANE-CONTAINING BISANHYDROHEXITOL DERIVATIVES AND USES THEREOF

CROSS REFERENCE TO RELATED APPLICATIONS

This application is a national stage filing under 35 U.S.C. 371 of PCT/US2012/068393, filed Dec. 7, 2012, which claims priority to U.S. Provisional Application No. 61/576,571, filed Dec. 16, 2011, the disclosure of which is incorporated by reference in its/their entirety herein.

TECHNICAL FIELD

Compounds that are bisanhydrohexitol derivatives having two terminal oxirane groups and the use of these compounds in both curable and cured compositions are described.

BACKGROUND

Current consumer demands, regulatory considerations, and dwindling sources of petroleum-based raw materials have created a need for alternative sources of materials as feedstocks for the preparation of polymeric materials.

Various plant based epoxy resins are known such those that are commercially available from Nagase Chemtex (Tokyo, Japan) under the trade designations EX-313, EX-512, and EX-521. Sorbitol polyglycidyl polyether is commercially available from CVC Thermoset Specialties (Moorestown, N.J., USA) under the trade designation ERISYS GE-60.

Various derivatives of bisanhydrohexitols (i.e., derivatives of isosorbide, isomannide, isoidide, or a mixture thereof) are known. For example, U.S. Pat. No. 6,608,167 (Hayest et al.) describes the use of bis(2-hydroxyethyl) isosorbide as a monomer in the preparation of various polyesters. U.S. Patent Application Publication 2010/0130759 (Gillet) describes various bisanhydrohexitol derivatives with terminal —$CH_2NH_2$ groups that can be used as monomers in the preparation of polyamides. U.S. Pat. No. 7,365,148 (Ono et al.) describes a polycarbonate prepared from bisanhydrohexitol. Isosorbide diglycidyl ethers are described in U.S. Pat. No. 3,272,845 (Zech et al.).

SUMMARY

Epoxy compounds that are bisanhydrohexitol derivatives (i.e., isosorbide derivatives, isomannide derivatives, isoidide derivatives, or mixtures thereof) having two terminal oxirane groups are provided. Additionally, curable compositions that include these epoxy compounds, cured compositions prepared from the curable compositions, and articles containing the cured compositions are described. The cured compositions can be used, for example, as a structural adhesive or as a coating.

In a first aspect, an epoxy compound that is a bisanhydrohexitol derivative with two terminal oxirane groups is provided. The epoxy compound is of Formula (I).

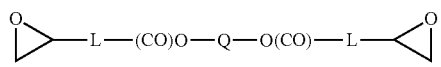
(I)

In Formula (I), each group L is a linear alkylene group and group Q is a divalent group of Formula (I-1), (I-2), or (I-3).

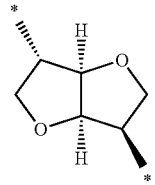
(I-1)

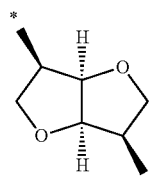
(I-2)

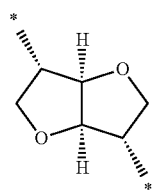
(I-3)

Each asterisk indicates an attachment point of the divalent group Q to the rest of the compound of Formula (I).

In a second aspect, a curable composition is provided that includes (a) an epoxy compound and (b) a curing agent. The epoxy compound is of Formula (I) as described above. That is, the epoxy compound is a bisanhydrohexitol derivative with two terminal oxirane groups In a third aspect, an article is provided that includes a first substrate and a cured composition positioned adjacent to the first substrate. The cured composition contains a reaction product of a curable composition that includes (a) an epoxy compound and (b) a curing agent. The epoxy compound is a compound of Formula (I) as described above. That is, the epoxy compound is a bisanhydrohexitol derivative with two terminal oxirane groups The above summary of the present invention is not intended to describe each embodiment or every implementation of the present invention. The Detailed Description and Examples that follow more particularly exemplify these embodiments.

DETAILED DESCRIPTION OF THE INVENTION

Epoxy compounds that are bisanhydrohexitol derivatives (i.e., isosorbide derivatives, isomannide derivatives, isoidide derivatives, or mixtures thereof) having two terminal oxirane groups are provided. Additionally, curable compositions that include these epoxy compounds, cured compositions prepared from the curable compositions, and articles containing the cured compositions are provided. The cured compositions can be used, for example, as a structural adhesive or as a coating.

In a first aspect, an epoxy compound that is a bisanhydrohexitol derivative with two terminal oxirane groups is provided. These epoxy compounds are of Formula (I).

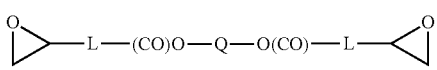
(I)

In Formula (I), each group L is a linear alkylene group and group Q is a divalent group of Formula (I-1), (I-2), or (I-3).

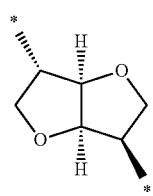
(I-1)

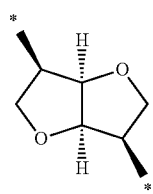
(I-2)

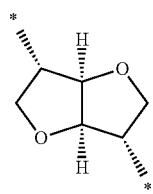
(I-3)

Each asterisk indicates an attachment point of the divalent group Q to the rest of the compound of Formula (I).

The compounds of Formula (I) can be referred to as epoxy compounds. The epoxy compounds have two terminal oxirane groups. As used herein, the term "oxirane" refers to the monovalent group of formula

where the asterisk indicates the site of attachment of the oxirane group to group L in Formula (I).

Each oxirane group is connected to group Q through an ester linkage of formula L-(CO)O—. Stated differently, the bisanhydrohexitol derivatives have two oxirane groups and two ester linkages. Group L is a linear alkylene having up to 30 carbon atoms, up to 20 carbon atoms, up to 18 carbon atoms, up to 16 carbon atoms, up to 12 carbon atoms, up to 10 carbon atoms, up to 8 carbon atoms, up to 6 carbon atoms, or up to 4 carbon atoms. Group L has at least 1 carbon atom, at least 2 carbon atoms, at least 4 carbon atoms, or at least 6 carbon atoms. In some embodiments, group L has 1 to 30 carbon atoms, 1 to 20 carbon atoms, 1 to 18 carbon atoms, 2 to 18 carbon atoms, 4 to 18 carbon atoms, 4 to 16 carbon atoms, 4 to 12 carbon atoms, or 8 to 12 carbon atoms. The two L groups per epoxy compound can be the same or different.

There are three stereoisomers of bisanhydrohexitol: isosorbide, isomannide, and isoidide. When group Q is of Formula (I-1), the epoxy compounds of Formula (I) are isosorbide derivatives of Formula (IA).

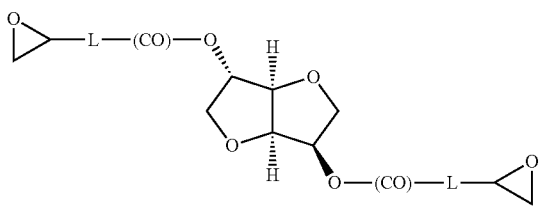
(IA)

When group Q is of Formula (I-2), the epoxy compounds of Formula (I) are isomannide derivatives of Formula (IB).

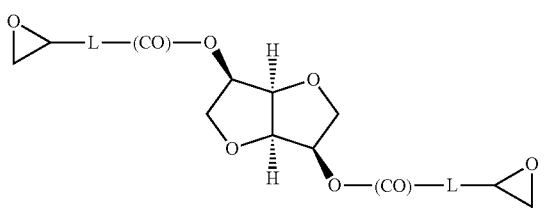
(IB)

When group Q is of Formula (I-3), the epoxy compounds of Formula (I) are isoidide derivatives of Formula (IC).

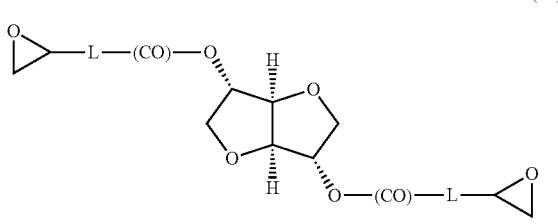
(IC)

The epoxy compounds of Formula (IA), Formula (IB), and Formula (IC) are stereoisomers. Each stereoisomer can be present individually or in a mixture with one or more of the other stereoisomers of Formula (I). In many embodiments, the epoxy compounds are of Formula (1A), which are isosorbide derivatives.

The epoxy compounds of Formulas (I) (i.e., the epoxy compounds of Formula (IA), (IB), (IC), or a mixture thereof) may be liquids or solids at room temperature (about 20° C. to about 25° C.) and are not liquid crystals.

The epoxy compounds of Formula (I) are di-esters that can be prepared using any method known in the art. For example, a method such as that shown in Reaction Scheme A can be used.

Reaction Scheme A

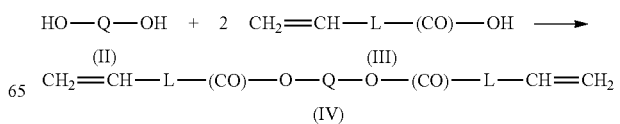

-continued

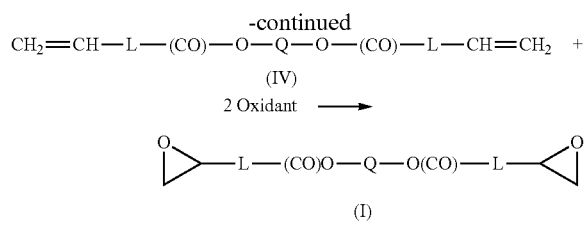

(I)

The compound of Formula (I) is a derivative of the bisanhydrohexitol of Formula (II), which can be a single stereoisomer or a mixture of the stereoisomers selected from isosorbide, isomannide, and isoidide. The various stereoisomers of bisanhydrohexitol are typically prepared from sugars such as those available from corn starch. For example, isosorbide can be formed from D-glucose (e.g., by hydrogenation followed by dehydration with an acid catalyst), isomannide can be formed from D-mannose, and isoidide can be formed from L-idose. The use of plant-based feedstocks rather than petroleum-based feedstocks can be desirable for many applications. That In contrast to petroleum-based feedstocks, plant-based feedstocks are renewable.

In Reaction Scheme A, an alkenyl acid (i.e., an alkenyl carboxylic acid) of Formula (III) is reacted initially with bisanhydrohexitol of Formula (II) to provide an intermediate of Formula (IV). Suitable alkenyl acids of Formula (III) have an ethylenically unsaturated group and have a group L as described above for Formula (I). Example compound of Formula (III) include but are not limited to, 10-undecenoic acid, 9-decenoic acid, 6-heptenoic acid, 4-pentenoic acid, and 3-butenoic acid. The molar ratio of hydroxyl groups to carboxylic acid groups is often in a range of 1:0.8 to 1:2. This reaction is often performed under reflux conditions in the presence of a strong acid catalyst such as, for example, sulfuric acid, p-toluene sulfonic acid, or methane sulfonic acid. The intermediate of Formula (IV) is then oxidized to form the epoxy compound of Formula (I). Suitable oxidants include, but are not limited to, peroxyformic acid, peroxybenzoic acid, 3-chloroperoxybenzoic acid, peroxyacetic acid, trifluoroperoxyacetic acid, and mixtures thereof.

In another aspect, curable compositions are provided that contain a) an epoxy compound of Formula (I) and b) a curing agent. The curable compositions can be applied as a coating to at least one surface of a substrate and then cured. In some embodiments, the cured compositions can be used as structural adhesives to bond together two surfaces (i.e., two substrate surfaces). The structural adhesives can be used, for example, to replace or augment conventional joining means such as welds or mechanical fasteners in bonding various surfaces together.

The curable compositions are often in the form of a two-part composition. The epoxy compound is typically separated from the curing agent prior to use of the curable composition. That is, the epoxy compound is typically in a first part and the curing agent is typically in a second part of the curable composition. The first part can include other components that do not react with the epoxy compound or that react with only a portion of the epoxy compound. Likewise, the second part can include other components that do not react with the curing agent or that react with only a portion of the curing agent. Various optional components such as a toughening agent, oil displacing agent, or filler can be included in the first part, in the second part, or in both the first part and the second part. When the first part and the second part are mixed together, the various components react to form the cured composition.

The epoxy compound of Formula (I) is included in the curable composition. In some embodiments, the epoxy compound of Formula (I) is the only epoxy compound included in the curable composition. In other embodiments, the curable composition includes a first epoxy compound of Formula (I) and a second epoxy compound. The second epoxy compound can be any known epoxy compound. The second epoxy compound can be added, for example, to provide the desired viscosity or flow characteristics to the curable composition. Alternatively, the first epoxy compound of Formula (I) can be added to a second epoxy compound to provide the desired flexibility to the cured composition. The second epoxy compound usually has 1 to 6 oxirane groups, 1 to 4 oxirane groups, or 1 to 3 oxirane group.

In some embodiments, the second epoxy compound is another plant-based compound. Suitable plant-based epoxy compounds are commercially available, for example, glycerol polyglycidyl ether from Nagase Chemtex (Tokyo, Japan) under the trade designation EX-313 and polyglycerol polyglycidyl ether from Nagase Chemtex under the trade designations EX-512 and EX-521. Epoxy resins based on cashew nutshell liquid under the trade designations NC-514 and NC-513 are available from Cardolite Corporation (Newark, N.J.). Further, bisanhydrohexitol-based epoxy compounds such as isosorbide diglycidyl ethers can be synthesized as described in U.S. Pat. No. 3,272,845 (Zech et al.). Sorbitol polyglycidyl polyether is commercially available from CVC Thermoset Specialties (Moorestown, N.J., USA) under the trade designation ERISYS GE-60 and from Nagase Chemtex under the trade designations EX-611, EX-612, and EX-622.

Some plant-based second epoxy compounds such as sorbital polyglycidyl polyethers (e.g., ERISYS GE-60 from CVC Thermoset Specialties) have high epoxy functionality (e.g., greater than 2, greater than 3, or greater than 4), low epoxy equivalent weight (e.g., less than 200 grams/equiveltn), and tend to cure into rigid but brittle cured compositions. The flexibility of the cured composition can be enhanced by combining these second epoxy compounds with an epoxy compound of Formula (I). If epoxy compound of Formula (I) is selected to be of Formula (IA) with a group L equal to —$(CH_2)_8$—, the epoxy compound has an epoxy functionality of 2 and an epoxy equivalent weight of 255 grams/equivalent. The epoxy compound of Formula (I) can be used to modulate the flexibility of cured compositions that include second epoxy compounds having greater than two oxirane groups per molecule and low epoxy equivalent weight (e.g., less than 200 grams/equivalent).

Other second epoxy compounds are petroleum-based materials. Suitable epoxy resins are typically a liquid at room temperature (e.g., about 20° C. to about 25° C.). However, second epoxy compounds that can be dissolved in a suitable solvent also can be used. In many embodiments, the second epoxy compound is a glycidyl ether. Example glycidyl ethers can be of Formula (V).

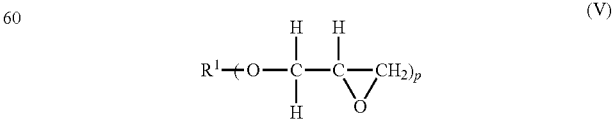

In Formula (V), group $R^1$ is a p-valent group that is aromatic, aliphatic, or a combination thereof. Group $R^1$ can be linear, branched, cyclic, or a combination thereof. Group $R^1$ can optionally include halo groups, oxy groups, thio groups, carbonyl groups, carbonyloxy groups, carbonylimino groups, phosphono groups, sulfono groups, nitro groups, nitrile groups, and the like. Although the variable p can be any suitable integer greater than or equal to 1, p is often an integer in the range of 2 to 10, in the range of 2 to 6, or in the range of 2 to 4.

In some example epoxy resins of Formula (V), the variable p is equal to 2 (i.e., the epoxy resin is a diglycidyl ether) and $R^1$ includes an alkylene (i.e., an alkylene is a divalent radical of an alkane and can be referred to as an alkane-diyl), heteroalkylene (i.e., a heteroalkylene is a divalent radical of a heteroalkane and can be referred to as a heteroalkane-diyl), arylene (i.e., a divalent radical of a arene compound, which is an aromatic hydrocarbon), heteroarylene (i.e., a divalent radical of a heteroarene compound, which is an aromatic compound having at least one heteroatom selected from oxygen, sulfur, or nitrogen), or combination thereof. Suitable alkylene groups often have 1 to 20 carbon atoms, 1 to 12 carbon atoms, 1 to 8 carbon atoms, or 1 to 4 carbon atoms. Suitable heteroalkylene groups often have 2 to 50 carbon atoms, 2 to 40 carbon atoms, 2 to 30 carbon atoms, 2 to 20 carbon atoms, 2 to 10 carbon atoms, or 2 to 6 carbon atoms with 1 to 10 heteroatoms, 1 to 6 heteroatoms, or 1 to 4 heteroatoms. The heteroatoms in the heteroalkylene can be selected from oxy, thio, or —NH— groups but are often oxy groups. Suitable arylene groups often have 6 to 18 carbon atoms or 6 to 12 carbon atoms. For example, the arylene can be phenylene or biphenylene. Suitable heteroarylene groups often have 3 to 18 carbon atoms or 3 to 12 carbon atoms. Group $R^1$ can further optionally include halo groups, oxy groups, thio groups, carbonyl groups, carbonyloxy groups, carbonylimino groups, phosphono groups, sulfono groups, nitro groups, nitrile groups, and the like. The variable p is usually an integer in the range of 2 to 4.

Some epoxy resins of Formula (V) are diglycidyl ethers where $R^1$ includes (a) an arylene group or (b) an arylene group in combination with an alkylene, heteroalkylene, or both. Group $R^1$ can further include optional groups such as halo groups, oxy groups, thio groups, carbonyl groups, carbonyloxy groups, carbonylimino groups, phosphono groups, sulfono groups, nitro groups, nitrile groups, and the like. These epoxy resins can be prepared, for example, by reacting an aromatic compound having at least two hydroxyl groups with an excess of epichlorohydrin. Examples of useful aromatic compounds having at least two hydroxyl groups include, but are not limited to, resorcinol, catechol, hydroquinone, p,p'-dihydroxydibenzyl, p,p'-dihydroxyphenylsulfone, p,p'-dihydroxybenzophenone, 2,2'-dihydroxyphenyl sulfone, and p,p'-dihydroxybenzophenone. Still other examples include the 2,2', 2,3', 2,4', 3,3', 3,4', and 4,4' isomers of dihydroxydiphenylmethane, dihydroxydiphenyldimethylmethane, dihydroxydiphenylethylmethylmethane, dihydroxydiphenylmethylpropylmethane, dihydroxydiphenylethylphenylmethane, dihydroxydiphenylpropylenphenylmethane, dihydroxydiphenylbutylphenylmethane, dihydroxydiphenyltolylethane, dihydroxydiphenyltolylmethylmethane, dihydroxydiphenyldicyclohexylmethane, and dihydroxydiphenylcyclohexane.

Some commercially available diglycidyl ether epoxy resins of Formula (V) are derived from bisphenol A (i.e., bisphenol A is 4,4'-(propane-2,2-diyl)diphenol). Examples include, but are not limited to, those available under the trade designation EPON (e.g., EPON 828, EPON 872, and EPON 1001) from Hexion Specialty Chemicals, Inc. (Houston, Tex., USA) those available under the trade designation D.E.R. (e.g., D.E.R. 331, DER 332, and D.E.R. 336) from Dow Chemical Co. (Midland, Mich., USA), and those available under the trade designation EPICLON (e.g., EPICLON 850) from Dainippon Ink and Chemicals, Inc. (Chiba, Japan). Other commercially available diglycidyl ether epoxy resins are derived from bisphenol F (i.e., bisphenol F is 2,2'-dihydroxydiphenylmethane). Examples include, but are not limited to, those available under the trade designation D.E.R. (e.g., D.E.R. 334) from Dow Chemical Co. and those available under the trade designation EPICLON (e.g., EPICLON 830) from Dainippon Ink and Chemicals, Inc.

Other epoxy resins of Formula (V) are diglycidyl ethers of a poly(alkylene oxide) diol. These epoxy resins also can be referred to as diglycidyl ethers of a poly(alkylene glycol) diol. The variable p is equal to 2 and $R^1$ is a heteroalkylene having oxygen heteroatoms. The poly(alkylene glycol) portion can be a copolymer or homopolymer and often include alkylene units having 1 to 4 carbon atoms. Examples include, but are not limited to, diglycidyl ethers of poly (ethylene oxide) diol, diglycidyl ethers of poly(propylene oxide) diol, and diglycidyl ethers of poly(tetramethylene oxide) diol. Epoxy resins of this type are commercially available from Polysciences, Inc. (Warrington, Pa., USA) such as those derived from a poly(ethylene oxide) diol or from a poly(propylene oxide) diol having a weight average molecular weight of about 400 grams/mole, about 600 grams/mole, or about 1000 gram/mole.

Still other epoxy resins of Formula (V) are diglycidyl ethers of an alkane diol ($R^1$ is an alkylene and the variable p is equal to 2). Examples include a diglycidyl ether of 1,4-cyclohexane dimethanol, diglycidyl ether of 1,4-butanediol, and diglycidyl ethers of the cycloaliphatic diol formed from a hydrogenated bisphenol A such as those commercially available under the trade designation EPONEX 1510 from Hexion Specialty Chemicals, Inc. (Columbus, Ohio, USA).

If the curable composition includes other epoxy compounds in addition to those of Formula (I), the curable composition contains at least 10 weight percent first epoxy compound of Formula (I) based on a total weight of epoxy compounds in the curable composition. For example, the curable composition can include at least 20 weight percent, at least 30 weight percent, at least 50 weight percent, at least 60 weight percent, at least 70 weight percent, at least 80 weight percent, or at least 90 weight percent first epoxy compound of Formula (I) based on a total weight of epoxy compounds in the curable composition.

The curable composition typically includes at least 20 weight percent epoxy compound (i.e., first epoxy compound plus any optional second epoxy compound) based on a combined weight of the epoxy compound and curing agent. For example, the curable composition can include at least 25 weight percent, at least 30 weight percent, at least 40 weight percent, or at least 50 weight percent epoxy compound. The curable composition often includes up to 90 weight percent epoxy compound. For example, the curable composition can include up 80 weight percent, up to 75 weight percent, up to 70 weight percent, up to 65 weight percent, or up to 60 weight percent epoxy compound. Some example curable compositions contain 20 to 90 weight percent, 20 to 80 weight percent, 20 to 70 weight percent, 30 to 90 weight percent, 30 to 80 weight percent, 30 to 70 weight percent, 30 to 60 weight percent, 40 to 90 weight percent, 40 to 80 weight percent, 40 to 70 weight percent, 50 to 90 weight percent, 50 to 80 weight percent, or 50 to 70 weight percent epoxy compound.

The epoxy compound is cured by reacting with a curing agent that is typically in a second part of the curable composition. Any suitable curing agent that is capable of opening the oxirane rings of the epoxy compound can be used. The curing agent is often (a) an amine compound having at least one primary amino group or at least one secondary amino group, (b) an imidazole, imidazoline, or salt thereof, (c) a phenol substituted with at least one group selected from a tertiary amino, secondary or tertiary alkyl, nitro, halo, hydroxyl, or combination thereof, (d) a bisphenol, (e) an anhydride, (f) a carboxylic acid, (g) a mercaptan, or (h) a mixture thereof.

Some suitable curing agents are amine compounds having at least one primary amino group or at least one secondary amino group. That is, the curing agent has at least one group of formula —NR$^2$H where R$^2$ is selected from hydrogen, alkyl, aryl, heteroaryl, alkylaryl, or alkylheteroaryl. Suitable alkyl groups often have 1 to 12 carbon atoms, 1 to 8 carbon atoms, 1 to 6 carbon atoms, or 1 to 4 carbon atoms. The alkyl group can be cyclic, branched, linear, or a combination thereof. Suitable aryl groups usually have 6 to 12 carbon atom such as a phenyl or biphenyl group. Suitable alkylaryl groups can be either an alkyl substituted with an aryl or an aryl substituted with an alkyl. The same aryl and alkyl groups discussed above can be used in the alkylaryl groups. Suitable heteroaryl groups are aromatic groups having a heteroatom such as oxygen, nitrogen, or sulfur. The heteroaryl often has up to 10 carbon atoms and up to 4 heteroatoms, up to 6 carbon atoms and up to 3 heteroatoms, or up to 4 carbon atoms and up to 2 heteroatoms. Suitable alkylheteroaryl groups can be either an alkyl substituted with a heteroaryl or a heteroaryl substituted with an alkyl. The same heteroaryl and alkyl groups discussed above can be used in the alkylheteroaryl groups. When the curing agent reacts with the epoxy compound, the oxirane group is opened and a covalent bond is formed linking the amine compound to the epoxy compound. The reaction results in the formation of divalent groups of formula —OCH$_2$—CH$_2$—NR$^2$— where R$^2$ is equal to hydrogen, alkyl, aryl, heteroaryl, alkylaryl, or alkylheteroaryl. The portion of the amine compound curing agent that is not an amino group can be any suitable aromatic group, aliphatic group, or combination thereof.

Some of the amine compounds useful as the curing agent are plant-based amines such as those having a single amino group of formula —NR$^2$H. Examples include, but are not limited to, dehydroabietylamine (DHAA), 2-aminomethyl-furan (FA), and difurylamines such as methylenebisfurylamine, ethylidenebisfurylamine, and 2-propylidenebisfurylamine. The difurylamines can be synthesized as described by Cawse et al., Makromol. Chem., 185, pp. 697-707 (1984) and U.S. Pat. No. 5,292,903 (Conner et al.). The use of these plant-based amines in combination with the bio-based epoxy compounds of Formula (I) can be used to provide renewable curable compositions.

Some amine compound curing agents are of Formula (VI). In some of these compounds, there are at least two primary amino groups, at least two secondary amino groups, or at least one primary amino group and at least one secondary amino group.

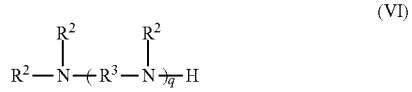

(VI)

Each R$^2$ group is independently hydrogen, alkyl, aryl, heteroaryl, alkylaryl, or alkylheteroaryl as described above. Each R$^3$ is independently an alkylene, heteroalkylene, or combination thereof. Suitable alkylene groups often have 1 to 18 carbon atoms, 1 to 12 carbon atoms, 1 to 8 carbon atoms, 1 to 6 carbon atoms, or 1 to 4 carbon atoms. Suitable heteroalkylene groups have at least one oxy, thio, or —NH— group positioned between two alkylene groups. Suitable heteroalkylene groups often have 2 to 50 carbon atoms, 2 to 40 carbon atoms, 2 to 30 carbon atoms, 2 to 20 carbon atoms, or 2 to 10 carbon atoms and with up to 20 heteroatoms, up to 16 heteroatoms, up to 12 heteroatoms, or up to 10 heteroatoms. The heteroatoms are often oxy groups. The variable q is an integer equal to at least one and can be up to 10 or higher, up to 5, up to 4, or up to 3.

Some amine curing agents of Formula (VI) can have an R$^3$ group selected from an alkylene group. Examples include, but are not limited to, ethylene diamine, diethylene diamine, diethylene triamine, triethylene tetramine, propylene diamine, tetraethylene pentamine, hexaethylene heptamine, hexamethylene diamine, 2-methyl-1,5-pentamethylene diamine, 1-amino-3-aminomethyl-3,3,5-trimethylcyclohexane (also called isophorene diamine), N',N'-1,5-bisfuranyl-2-methylmethylene-pentane-1,5-diamine (TEKA), and the like. Other amine curing agents can have an R$^3$ group selected from a heteroalkylene group such as a heteroalkylene having oxygen heteroatoms. For example, the curing agent can be a compound such as aminoethylpiperazine, 4,7,10-trioxatridecane-1,13-diamine (TTD) available from TCI America (Portland, Oreg., US), or a poly(alkylene oxide)diamine (also called a polyether diamine) such as a poly(ethylene oxide)diamine, poly(propylene oxide)diamine, or a copolymer thereof. Commercially available polyether diamines are commercially available under the trade designation JEFFAMINE from Huntsman Corporation (The Woodlands, Tex., USA).

Still other amine curing agents can be formed by reacting a polyamine (i.e., a polyamine refers to an amine with at least two amino groups selected from primary amino groups and secondary amino groups) with another reactant to form an amine-containing adduct having at least two amino groups. For example, a polyamine can be reacted with an epoxy compound to form an adduct having at least two amino groups. If a polymeric diamine is reacted with a dicarboxylic acid in a molar ratio of diamine to dicarboxylic acid that is greater than or equal to 2:1, a polyamidoamine having two amino groups can be formed. In another example, if a polymeric diamine is reacted with an epoxy compound having two glycidyl groups in a molar ratio of diamine to epoxy compound greater than or equal to 2:1, an amine-containing adduct having two amino groups can be formed. Such a polyamidoamine can be prepared as described, for example, in U.S. Pat. No. 5,629,380 (Baldwin et al.). A molar excess of the polymeric diamine is often used so that the curing agent includes both the amine-containing adduct plus free (non-reacted) polymeric diamine. For example, the molar ratio of diamine to epoxy compound with two glycidyl groups can be greater than 2.5:1, greater than 3:1, greater than 3.5:1, or greater than 4:1. Even when epoxy compound is used to form the amine-containing adduct in the second part of the curable composition, additional epoxy compound is present in the first part of the curable composition.

Other curing agents can be imidazoles, imidazolines, or salts thereof. Examples include, but are not limited to, 2-methylimidazole, 2-hydroxypropylimidazole, 2-heptadecylimidazole, 2-ethyl-4-methylimidazole, 1-benzyl-2-methylimidazole, and the like. Some example imidazoles are commercially available under the trade designation CUREZOL and IMICURE from Air Products and Chemicals Inc. (Allentown, Pa., USA) and EPICURE P-101 from Momentive Specialty Chemicals (Houston, Tex., USA).

Still other curing agents are phenols substituted with at least one group selected from a tertiary amino, tertiary alkyl, secondary alkyl, nitro, halo, hydroxyl, or combination thereof. Example phenols substituted with tertiary amino groups can be of Formula (VII).

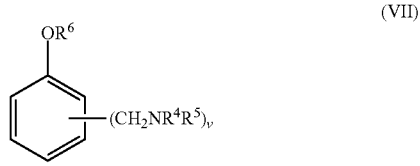

(VII)

In Formula (VII), each group $R^4$ and $R^5$ is independently an alkyl. The variable v is an integer equal to 2 or 3. Group $R^6$ is hydrogen or alkyl. Suitable alkyl groups for $R^4$, $R^5$, and $R^6$ often have 1 to 12 carbon atoms, 1 to 8 carbon atoms, 1 to 6 carbon atoms, or 1 to 4 carbon atoms. One example curative of Formula (VII) is tris-2,4,6-(dimethylaminomethyl)phenol that is commercially available under the trade designation ANCAMINE K54 from Air Products Chemicals, Inc. (Allentown, Pa., USA). Other example phenols not of Formula (VII) include, but are not limited to, 4-tert-butylphenol, nonylphenol, 2-nitrophenol, 4-nitrophenol, 2-chlorophenol, 4-chlorophenol, and catechol.

Bisphenol curing agents include, for example, bisphenol A (i.e., 4,4'-(propane-2,2-diyl)diphenol), bisphenol F (i.e., bis(4-hydroxyphenyl)methane), and 2,2'-bisphenol. Suitable anhydride curing agents include benzophenone tetracarboxylic acid anhydride, succinic anhydride, maleic anhydride, phthalic anhydride, and the like. Suitable carboxylic acid curing agents include adipic acid, sebacic acid, terephthalic acid, isophthalic acid, salicylic acid, valeric acid, 2,4-dichlorobenzoic acid, and the like.

A range of concentrations can be used for the curing agent depending on the curing temperature. In many embodiments, if low curing temperatures are used, more of the curing agent is included in the curable composition. If the curing reaction occurs at room temperature, the ratio of curing agent hydrogen equivalent weight to epoxy equivalent weight in the curable composition is often at least 0.5:1, at least 0.8:1, or at least 1:1. The ratio can up be to 2:1, up to 1.5:1, up to 1.2:1, or up to 1.1:1. For example, the ratio can be in the range of 0.5:1 to 2:1, in the range of 0.5:1 to 1.5:1, in the range of 0.8:1 to 2:1, in the range of 0.8:1 to 1.5:1, in the range of 0.8:1 to 1.2:1, in the range of 0.9:1 to 1.1:1, or about 1:1.

Alternatively, if higher curing temperatures are used such as at least 80° C., less of the curing agent is included in the curable composition. The amount of the curing agent in the curable composition is often present in a molar amount to react with only a portion of the epoxy compound. For example, the ratio of curing agent hydrogen equivalent weight to epoxy equivalent weight is often less than 1:1 such in the range of 0.2:1 to 0.8:1, in the range of 0.2:1 to 0.6:1, or in the range of 0.3:1 to 0.5:1. Any epoxy compound that is not reacted with the curing agent tends to undergo homopolymerization at elevated temperatures.

The curable composition typically includes at least 20 weight percent curing agent based on a combined weight of the epoxy compound and curing agent. For example, the curable composition can include at least 25 weight percent, at least 30 weight percent, at least 40 weight percent, or at least 50 weight percent curing agent. The curable composition often includes up to 90 weight percent curing agent. For example, the curable composition can include up 80 weight percent, up to 75 weight percent, up to 70 weight percent, up to 65 weight percent, or up to 60 weight percent curing agent. Some example curable compositions contain 20 to 90 weight percent, 20 to 80 weight percent, 20 to 70 weight percent, 30 to 90 weight percent, 30 to 80 weight percent, 30 to 70 weight percent, 30 to 60 weight percent, 40 to 90 weight percent, 40 to 80 weight percent, 40 to 70 weight percent, 50 to 90 weight percent, 50 to 80 weight percent, or 50 to 70 weight percent curing agent.

Some curable compositions contain 20 to 80 weight percent epoxy compound and 20 to 80 weight percent curing agent based on a combined weight of the epoxy compound and curing agent. For example, the curable composition can include 30 to 70 weight percent epoxy compound and 30 to 70 weight percent curing agent or 40 to 60 weight percent epoxy compound and 40 to 60 weight percent curing agent.

The curable compositions optionally can include a toughening agent. Toughening agents are polymers other than the curable epoxy compounds that are capable of enhancing the toughness of the cured composition. The toughening agents can be added to the first part of the curable composition with the epoxy compound, to the second part of the curable composition with the curing agent, or to both the first and second part of the curable composition. Typical toughening agents include core-shell polymers, butadiene-nitrile rubbers, acrylic polymers and copolymers, and the like.

Some toughening agents are core-shell polymers. A shell polymeric material is typically grafted to a core polymeric material. The core is usually an elastomeric material with a glass transition temperature less than 0° C. The shell is usually a polymeric material having a glass transition temperature greater than 25° C. The glass transition temperature can be determined using dynamic mechanical thermal analysis (DMTA) or a similar method.

The core of the core-shell polymeric toughening agents is often prepared from a butadiene polymer or copolymer, a styrene polymer or copolymer, an acrylonitrile polymer or copolymer, an acrylate polymer or copolymer, or combinations thereof. These polymers or copolymers can be cross-linked or not crosslinked. Some example cores are polymethylmethacrylates that are either crosslinked or not crosslinked. Other example cores are butadiene-styrene copolymers that are either crosslinked or not crosslinked.

The shell of the core-shell polymeric toughening agents are often formed from a styrene polymer or copolymer, a methacrylate polymer or copolymer, an acrylonitrile polymer or copolymer, or combinations thereof. The shell can be further functionalized with epoxy groups, acidic groups, or acetoacetoxy groups. Functionalization of the shell may be achieved, for example, by copolymerization with glycidylmethacrylate or acrylic acid or by reaction of a hydroxyl group with an alkyl acetoacetoxy such as tert-butyl acetoacetoxy. The addition of these functional groups can result in the shell being crosslinked into the polymeric matrix.

Suitable core-shell polymers often have an average particle size equal to at least 10 nanometers, at least 20 nanometers, at least 50 nanometers, at least 100 nanometers, at least 150 nanometers, or at least 200 nanometers. The average particle size can be up to 400 nanometers, up to 500 nanometers, up to 750 nanometers, or up to 1000 nanometers. The average particle size can be, for example, in the range of 10 to 1000 nanometers, in the range of 50 to 1000 nanometers, in the range of 100 to 750 nanometers, or in the range of 150 to 500 nanometers.

Example core-shell polymers and their preparation are described in U.S. Pat. No. 4,778,851 (Henton et al.). Commercially available core-shell polymers can be obtained, for example, under the trade designation PARALOID (e.g., PARALOID EXL 2600 and PARALOID EXL 2691) from Rohm & Haas Company (Philadelphia, Pa., USA) and under the trade designation KANE ACE (e.g., KANE ACE B564, KANE ACE MX120, KANE ACE MX257, and KANE ACE MX153) from Kaneka (Belgium).

Still other toughening agents can be prepared by reacting amino-terminated materials or carboxy-terminated materials with an epoxy compound to prepare an adduct that phase separates from the other components in the cured composition. Suitable amino-terminated materials that can be used to prepare such toughening agents include, but are not limited to, those commercially available under the trade designation DYNAMAR POLYETHERDIAMINE HC 1101 from 3M Corporation (Saint Paul, Minn., USA). This is a linear polymeric material. Suitable carboxy-terminated materials include carboxy-terminated butadiene acrylonitrile copolymers such as those commercially available from Emerald Chemical (Alfred, Me., USA).

Various optional accelerators such as various metal salts can be added. Useful metal salts include, for example, calcium ($Ca^{+2}$) salts, magnesium ($Mg^{+2}$) salts, bismuth ($Bi^{+3}$) salts, cerium ($Ce^{+3}$) salts, iron salts ($Fe^{+3}$), lead ($Pb^{+1}$) salts, copper ($Cu^{+2}$) salts, cobalt ($Co^{+2}$) salts, lanthanum ($La^{+3}$) salts, lithium ($Li^{+1}$) salts, indium ($In^{+3}$) salts, thallium ($Th^{+4}$) salts, beryllium ($Be^{+2}$) salts, barium ($Ba^{+2}$) salts, strontium ($Sr^{+2}$) salts, and zinc ($Zn^{+2}$) salts. In many embodiments, the accelerators are selected to be calcium salts, magnesium salts or lanthanum salts. Suitable anions of the metal salts include, but are not limited to, $NO_3^-$, $CF_3SO_3^-$, $ClO_4^-$, $BF_4^-$, $CH_3C_6H_4SO_3^-$, and $SbF_6^-$.

Other optional components such as fillers can be added to the curable compositions. The fillers can be added to the first part of the curable composition, to the second part of the curable composition, or to both the first part and the second part of the curable composition. Fillers are often added to promote adhesion, to improve corrosion resistance, to control the rheological properties, to reduce shrinkage during curing, to accelerate curing, to absorb contaminants, to improve heat resistance, or for a combination thereof. The fillers can be inorganic material, organic materials, or composite materials containing both inorganic and organic materials. The fillers can have any suitable size and shape. Some fillers are in the form of particles with spherical, elliptical, or platelet shapes. Other fillers are in the form of fibers.

Some fillers are inorganic fibers such as fiber glass (e.g., glass wool and glass filament), mineral wool (e.g., rock wool and slag wool), and refractory ceramic fibers. Some example inorganic fibers include a mixture of $SiO_2$, $Al_2O_3$, or a combination thereof. The inorganic fibers can further include CaO, MgO, $Na_2O$, $K_2O$, $Fe_2O_3$, $TiO_2$, other oxides, or mixtures thereof. Example inorganic fibers are commercially available under the trade designation COATFORCE (e.g., COATFORCE CF50 and COATFORCE CF10) from Lapinus Fibres BV (Roermond, The Netherlands). Other example inorganic fibers can be prepared from wollastonite (i.e., calcium silicate).

Other fillers are organic fibers such as aramid fibers and polyolefin fibers such as polyethylene fibers. These organic fibers can be untreated or treated to change their hydrophobic or hydrophilic character. For example, some organic fibers are specially treated to make them hydrophobic or to increase their hydrophobicity. The fibers can be fibrillated. Example polyolefin fibers include high-density polyethylene fibers such as those available under the trade designation SYLOTHIX (e.g., SYLOTHIX 52 and SYLOTHIX 53) from EP Minerals (Reno, Nev., USA), those available under the trade designation ABROTHIX (e.g., ARBOTHIX PE100) from EP Minerals, those available under the trade designation SHORT STUFF (e.g., SHORT STUFF ESS2F and SHORT STUFF ESS5F) from MiniFIBERS, Inc. (Johnson City, Tenn., USA), and those available under the trade designation INHANCE (e.g., INHANCE PEF) from Inhance/Fluoro-Seal, Limited (Houston, Tex., USA). Example aramid fibers are commercially available under the trade designation INHANCE (e.g., INHANCE KF) from Inhance/Fluoro-Seal, Ltd. (Houston, Tex., USA).

Other suitable fillers include silica-gels, calcium silicates, calcium nitrate, calcium phosphates, calcium molybdates, calcium carbonate, calcium hydroxide, fumed silica, clays such as bentonite, organo-clays, aluminium trihydrates, glass microspheres, hollow glass microspheres, polymeric microspheres, and hollow polymeric microspheres. The fillers can also be a pigment such as ferric oxide, brick dust, carbon black, titanium oxide, and the like. Any of these filler can be surface modified to make them more compatible with the curable or cured composition.

Example fillers include a mixture of synthetic amorphous silica and calcium hydroxide that is commercially available from W.R. Grace (Columbia, Md., USA) under the trade designation SHIELDEX (e.g., SHIELDEX AC5), a fumed silica treated with polydimethylsiloxane to prepare a hydrophobic surface that is available from Cabot GmbH (Hanau, Germany) under the trade designation CAB-O-SIL (e.g., CAB-O-SIL TS 720), a hydrophobic fumed silica available from Degussa (Dusseldorf, Germany) under the trade designation AEROSIL (e.g., AEROSIL VP-R-2935), glass beads class IV (250 to 300 micrometers) from CVP S.A. (France), and epoxysilane-functionalized (2 wt %) aluminium trihydrate available under the trade designation APYRAL 24ES2 from Nabaltec GmbH (Schwandorf, Germany).

The curable composition can include an optional adhesion promoter. Example adhesion promoters include, but are not limited to, various silane compounds. Some silane compounds that are suitable for adhesion promoters have amino groups or glycidyl groups that can react with one or more components in the curable composition. One such silane compound is a glycidoxypropyltrimethoxysilane that is commercially available under the trade designation SILANE Z6040 from Dow Corning (Midland, Mich., USA). Other example adhesive promoters include various chelating agents such as those described in U.S. Pat. No. 6,632,872 (Pellerite et al.) and various chelate-modified epoxy compounds such as those available from Adeka Corporation (Tokyo, Japan) under the trade designation EP-49-10N and EP-49-20.

Solvents optionally can be included in the curable composition. The solvents are typically selected to be miscible with the curable composition. Solvents can be added to lower the viscosity of either the first part or the second part of the curable composition or can be added with one of the various components included in the curable composition. The amount of solvent is typically minimized and is often less than 15 weight percent based on a total weight of the curable composition. The solvent is often less than 12 weight percent, less than 10 weight percent, less than 8 weight percent, less than 6 weight percent, less than 4 weight percent, less than 2 weight percent, less than 1 weight percent, or less than 0.5 weight percent based on the total weight of the curable composition. Suitable organic solvents include those that are soluble in the curable composition and that can be removed during or after curing to form the cured composition. Example organic solvents include, but are not limited to, toluene, acetone, various alcohols, and xylene.

The curable composition typically is in the form of a first part and a second part. The first part typically includes the epoxy compounds plus other components that do not react with the epoxy compound. The second part typically includes the curing agent plus any other components that do not react with the curing agent. The components in each part are typically selected to minimize reactivity within that part.

The various parts of the curable composition are mixed together to form the cured composition. These parts are typically mixed together immediately prior to use of the curable composition. The amount of each part included in the mixture can be selected to provide the desired molar ratio of oxirane groups to curing agent hydrogen atoms.

The curable composition can be cured at room temperature, can be cured at room temperature and then at an elevated temperature (e.g., at least 80° C., at least 100° C., at least 120° C., or at least 150° C.), or can be cured at an elevated temperature. In some embodiments, the curable composition can be cured at room temperature for at least 3 hours, at least 6 hours, at least 12 hours, at least 18 hours, at least 24 hours, at least 48 hours, or at least 72 hours. In other embodiments, the curable composition can be cured at room temperature for any suitable length of time and then further cured at an elevated temperature such as, for example, 180° C. for a time up to 10 minutes, up to 20 minutes, up to 30 minutes, up to 60 minutes, up to 120 minutes, or even longer than 120 minutes.

In another aspect, an article is provided that includes a first substrate and a cured composition positioned adjacent to the first substrate. The cured composition contains a reaction product of a curable composition that includes (a) an epoxy compound of Formula (I) and (b) a curing agent. Suitable substrates onto which the curable composition can be applied include metals (e.g., steel, iron, copper, aluminum, or alloys thereof), carbon fiber, glass fiber, glass, epoxy fiber composites, wood, polymeric materials, and mixtures thereof.

The cured compositions may be used as an adhesive such as a structural adhesive. The cured compositions may be used to supplement or completely eliminate a weld or mechanical fastener by applying the curable composition between two parts (i.e., between two surfaces of two substrates) to be joined and curing the adhesive to form a bonded joint. In some embodiments, at least one of the substrates is a metal. In other embodiments, both substrates are metal. Alternatively, the cured compositions can be used to provide a polymeric coating on a substrate.

When used as an adhesive, the cured composition can be augmented by welding or mechanical fastening. The welding can occur as spot welds, as continuous seam welds, or as any other welding technology that can cooperate with the adhesive composition to form a mechanically sound joint. In some embodiments, the structural adhesives are used in vehicle assembly, in architectural applications, or in various household and industrial appliances.

The curable composition can be applied as liquid, paste, spray, or solid that can be liquefied upon heating. The application can be as a continuous bead or as dots, stripes, diagonals or any other geometrical form that will result in the formation of a useful bond. In some embodiments, the curable composition is in a liquid or paste form.

In another aspect, a method of making a composite article is provided. The method includes applying a two-part curable composition to a substrate, and curing the two-part curable adhesive while in contact with the substrate to form a composite article. The resulting cured composition can function as a polymeric coating for the substrate.

In yet another aspect, a method of forming a bonded joint between substrates is provided. The method includes applying a two-part curable composition to a surface of at least one of two or more substrates, joining the substrates so that the two-part curable composition is positioned between the two or more substrates, and curing the curable composition to form a bonded joint between the two or more substrates.

The cured compositions often have a glass transition temperature that is higher than other known cured compositions containing other plant-based epoxy compounds such as plant-based epoxy resins that are derivatives of glycerol.

Various items are provided that are compounds, curable compositions, or articles.

Item 1 is a compound of Formula (I).

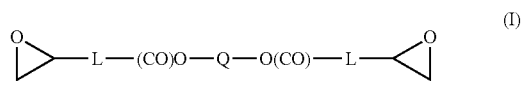

In Formula (I), the group L is a linear alkylene group and the group Q is a divalent group of Formula (I-1), (I-2), or (I-3).

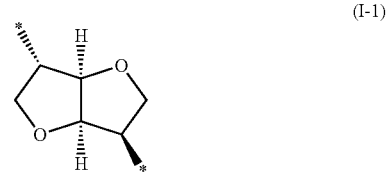

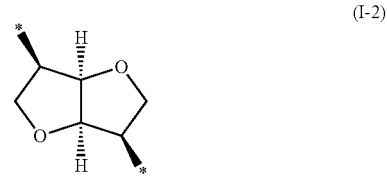

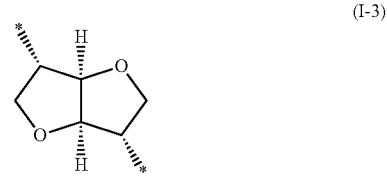

Item 2 is the compound of item 1, wherein the compound of Formula (I) is of Formula (IA).

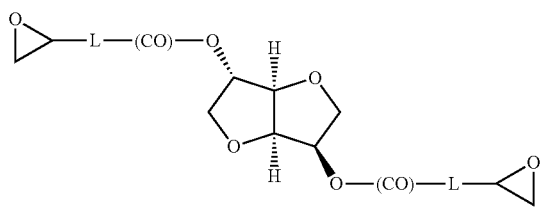

(IA)

Item 3 is the compound of item 1 or 2, wherein L has 1 to 30 carbon atoms.

Item 4 is the compound of any one of items 1 to 3, wherein L has 4 to 20 carbon atoms.

Item 5 is a curable composition comprising (a) a first epoxy compound of Formula (I)

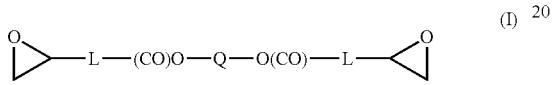

(I)

and (b) a curing agent. In Formula (I), the group L is a linear alkylene group and the group Q is a divalent group of Formula (I-1), (I-2), or (I-3).

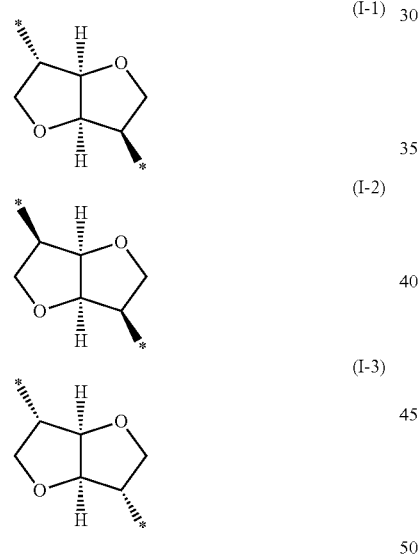

Item 6 is the curable composition of item 5, wherein the compound of Formula (I) is of Formula (IA).

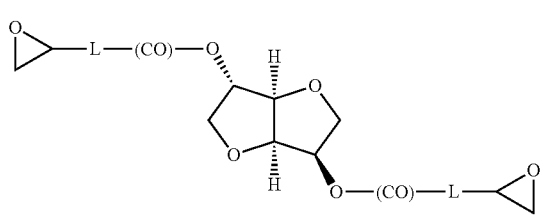

(IA)

Item 7 is the curable composition of item 5 or 6, wherein the curing agent comprises (a) an amine compound having at least one primary amino group or at least one secondary amino group, (b) an imidazole, imidazoline, or salt thereof, (c) a phenol substituted with at least one group selected from a tertiary amino, secondary or tertiary alkyl, nitro, halo, hydroxyl, or combination thereof, (d) a bisphenol, (e) an anhydride, (f) a carboxylic acid, (g) a mercaptan, or (h) a mixture thereof.

Item 8 is the curable composition of any one of items 5 to 7, further comprising a second epoxy compound that is not of Formula (I).

Item 9 is the curable composition of item 8, wherein the second epoxy compound is a plant-based epoxy compound.

Item 10 is the curable composition of item 8, wherein the second epoxy compound is a diglycidyl ether derivative of bisphenol A or a diglycidyl ether derivative of bisphenol F.

Item 11 is an article comprising a first substrate and a cured composition positioned adjacent to the first substrate. The curable composition comprises (a) a first epoxy compound of Formula (I)

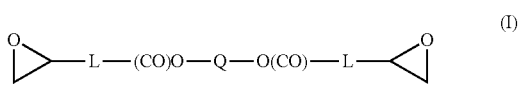

(I)

and (b) a curing agent. In Formula (I), the group L is a linear alkylene group and the group Q is a divalent group of Formula (I-1), (I-2), or (I-3).

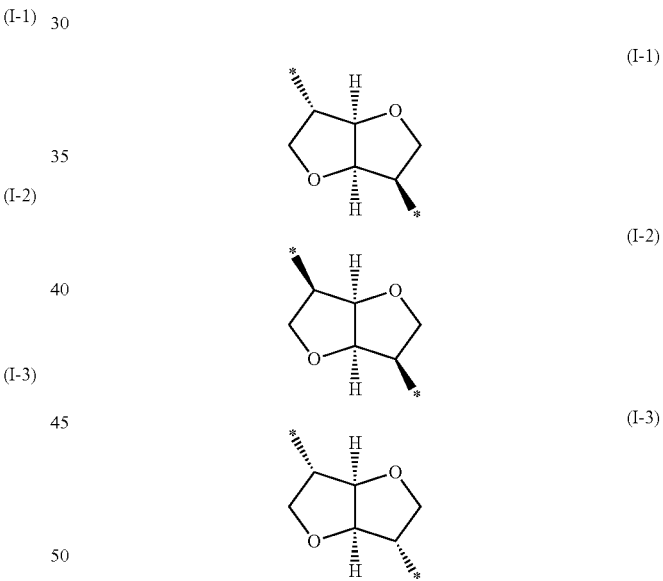

Item 12 is the article of item 11, wherein the compound of Formula (I) is of Formula (IA).

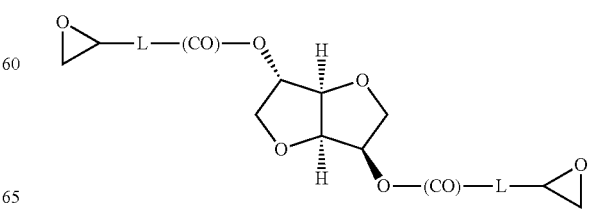

(IA)

Item 13 is the article of item 11 or 12, wherein the curing agent comprises (a) an amine compound having at least one primary amino group or at least one secondary amino group, (b) an imidazole, imidazoline, or salt thereof, (c) a phenol substituted with at least one group selected from a tertiary amino, secondary or tertiary alkyl, nitro, halo, hydroxyl, or combination thereof, (d) a bisphenol, (e) an anhydride, (f) a carboxylic acid, (g) a mercaptan, or (h) a mixture thereof.

Item 14 is the article of any one of items 11 to 13, wherein the cured composition is a coating on the substrate.

Item 15 is the article of any one of items 11 to 13, wherein the article has two substrates and the curable composition is a structural adhesive bonding the two substrates together.

EXAMPLES

The particular materials and amounts thereof recited in these examples, as well as other conditions and details, should not be construed as being unduly limiting. These examples are merely for illustrative purposes and are not meant to be limiting on the scope of the appended claims.

Materials Used

Solvents and other reagents used can be obtained from Sigma-Aldrich Chemical Company (Saint Louis, Mo., USA) unless otherwise noted.

The alkenyl acid 10-undecenoic acid was obtained Alfa Aesar (Ward Hill, Pa., USA).

The alkenyl acid 9-decenoic acid was obtained from Oakwood Products Inc. (West Columbia, S.C., USA).

Technical grade tris-2,4,6-dimethylaminomethyl-phenol was obtained from Air Products and Chemicals, Inc. (Allentown, Pa., USA) under the trade designation ANCAMINE K54 (K54).

The compound 2-aminomethylfuran (FA) was obtained from Alfar Aesar (Ward Hill, Mass., USA).

Bisphenol A (BPA), which is 4,4'-(propane-2,2-diyl)diphenol, was obtained from Alfa Aesar (Ward Hill, Mass., USA).

CELITE is a trade designation of Fluka, Sigma-Aldrich Corp. (St. Louis, Mo., USA) for a diatomaceous earth filter aide.

Dehydroabietylamine (DHAA) is a rosin acid derivative that was obtained from TCI America (Portland, Oreg., USA).

D.E.R. 331 is a trade designation of Dow Chemical Company (Midland, Mich., USA) for a liquid epoxy resin with an average epoxy equivalent weight of 187. The epoxy resin is a reaction product of bisphenol A and epichlorohydrin.

DFA is ethylidenebisfurylamine having amine hydrogen equivalent weight of 48.6 grams/equivalent.

It is synthesized as described by Cawse et al., "Polymers from Renewable Sources, 1: Diamines and Diisocyanates Containing Difurylalkane Moieties", Makromol. Chem., 185, 697-707 (1984).

DFA II is 2-propylidenebisfurylamine having amine hydrogen equivalent weight of 58.6 grams/equivalent.

It is synthesized as described in U.S. Pat. No. 5,292,903 (Conner et al.).

DTA is a multifunctional dimer diamine with an amine hydrogen equivalent weight of 137. It is commercially available from Croda, USA Inc. (Edison, N.J., USA).

The compound 2-methylpentamethylenediamine is commercially available under the trade designation DYTEK A from Invista (Wilmington, Del., USA).

Furfural was obtained from Alfa Aesar (Ward Hill, Mass., USA).

Isophorone diamine (IPDA) was obtained from TCI America (Portland, Oreg., USA).

Isosorbide was obtained from Roquette America Inc. (Geneva, Ill., USA).

Maleic anhydride (MA) was obtained from TCI America (Portland, Oreg., USA).

Platinum (5 weight percent on activated carbon) was obtained from Sigma-Aldrich (Saint Louis, Mo., USA).

Platinum (IV) oxide, $PtO_2$, was obtained from Alfa Aesar (Ward Hill, Pa., USA).

The strong acid p-toluene sulfonic acid hydrate was obtained from Alfa Aesar (Ward Hill, Pa., USA).

Sorbitol polyglycidyl polyether with an epoxy equivalent weight of 195 was obtained from CVC Thermoset Specialties (Moorestown, N.J., USA) under the trade designation ERISYS GE-60.

The compound N',N'-1,5-bisfuranyl-2-methylmethylenepentane-1,5-diamine (TEKA) with an amine hydrogen equivalent weight of 138.2 grams/equivalent was synthesized.

In a Parr pressure vessel (Parr Instrument Co., Moline, Ill., USA), platinum oxide (200 milligrams) was added to ethanol (200 mL). The vessel was evacuated and filled with hydrogen three times. The vessel was refilled to 60 pounds per square inch (psi) (0.41 Mpa) with hydrogen and then rocked for 1 hour to pre-reduce the catalyst. The vessel was then evacuated and refilled with nitrogen three times. Furfural (35.00 grams, 0.36 moles) and DYTEK A (21.23 grams, 0.18 moles) were added. The vessel was evacuated and refilled with hydrogen three times. The vessel was then filled with hydrogen to 60 (psi) (0.41 Mpa) and rocked at room temperature for 1 week. The vessel was evacuated and refilled with nitrogen three times and then 10 weight percent platinum on carbon (100 milligrams) was added. The vessel was evacuated and refilled three times with hydrogen. The vessel was then filled with hydrogen to 60 psi and rocked for 3 days. The vessel was evacuated and refilled with nitrogen three times. The mixture was then filtered through CELITE and concentrated under vacuum overnight to yield the desired product as a brown oil (50.72 grams).

Generation of Overlap Shear Bonds

Overlap shear bond test specimens were made using cleaned, cold-rolled steel panels. The panels were cleaned three times with toluene followed by another three times with acetone. The panels were obtained from Q-Lab Corporation (Cleveland, Ohio, USA) and were iron phosphate (B-1000) steel panels (type "RS" steel) having square corners and measuring 4 inch×1 inch×0.063 inch (10.2 cm×2.54 cm×0.16 cm). The test specimens were generated as described in ASTM Specification D 1002-05. An adhesive strip that was approximately 0.5 inches (1.27 cm) wide and 0.010 inch (0.254 mm) thick was applied to one edge of each of two steel panels using a wooden scraper. Glass beads (approximately 250 micrometers in diameter) were sprinkled throughout the adhesive and served as spacers. The bond was closed and clamped using a 1 inch (2.54 cm) binder clip to apply pressure to provide for adhesive spreading. After the adhesive had been allowed to cure (as described in the examples), the bonds were tested to failure at room temperature on a Sintech Tensile Testing machine obtained from MTS (Eden Prairie, Minn., USA) using a crosshead displacement rate of 0.1 inch/minute (2.54 mm/minute). The failure load was recorded. The lap width was measured with a Vernier caliper. The quoted lap shear strengths were calculated as failure load divided by measured bond area. The average and standard deviation were calculated from the results of at least three tests unless otherwise noted.

Adhesive Preparation

All adhesive samples were prepared by mixing the epoxy compound with the curing agent thoroughly in a plastic cup using a DAC 400 high speed mixer, which can be obtained from FlackTek, Inc. (Landrum, S.C., USA). Unless otherwise stated, overlap shear bond test specimens were prepared from the adhesives as described above.

Differential Scanning Calorimetry (DSC) Analysis

Cure temperature and glass transition temperature were determined by differential scanning calorimetry using a Model DSC Q200 instrument available from TA Instruments (New Castle, Del., USA). For cure temperature determination, the liquid mixture (approximately 10 milligrams) was placed into hermetic aluminum DSC pans and crimped to seal. The sample was heated at a rate of 10° C./minute from 20° C. to 300° C. under nitrogen flow (50 mL/minute). The temperature at the peak maximum of the resulting heat flow versus temperature curve was noted as the cure temperature.

The liquid composition was cured under ambient conditions (approximately 23° C.) for 7 days to obtain a solid sample. Approximately 10 mg of the solid sample was placed into hermetic aluminum pan and sealed. The glass transition temperature ($T_g$) was determined by heating at a rate of 10° C./minute from −50° C. to 300° C. under nitrogen flow (50 mL/minute).

Example 1

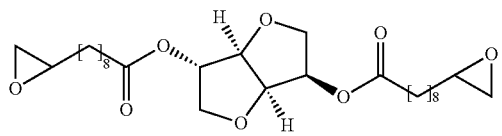

A mixture of 10-undecenoic acid (110.73 grams, 0.60 moles), isosorbide (40.00 g, 0.27 moles), toluene (400 mL), and p-toluene sulfonic acid hydrate (1.60 grams) was heated to reflux for 17 hours. The water that separated was collected using a Dean-Stark trap. The mixture was cooled and then diluted with ethyl acetate (300 mL). The mixture was then washed with 1.0 M sodium hydroxide solution (100 mL) and brine (100 mL). The organic phase was separated and concentrated under vacuum to give a yellow, crude oil. The crude oil was filtered through a bed of neutral alumina and eluted with a mixture of ethyl acetate and hexane (1:5 by volume). The filtrate was concentrated to give a yellow oil (82.47 grams).

The oil prepared above (20.00 grams, 42 mmoles) was mixed with dichloromethane (200 mL). 3-chloroperbenzoic acid (20.6 grams, 85 mmoles, 70 weight percent in water, Sigma-Aldrich, St. Louis, Mo., USA) was added portion-wise over 5 minutes. The mixture was stirred for 17 hours at room temperature and then filtered. The mixture was washed with 1.0 M sodium hydroxide solution (70 mL) and brine (50 mL). The organic phase was separated and concentrated under vacuum to give a colorless oil that slowly crystallized into a white solid (16.02 grams).

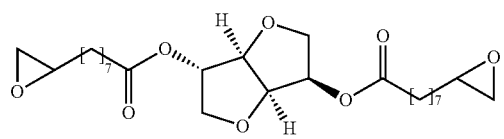

Example 2

A mixture of 9-decenoic acid (70.00 grams, 0.45 moles), isosorbide (29.90 grams, 0.20 moles), toluene (300 mL), and p-toluene sulfonic acid hydrate (1.20 grams) was heated to reflux for 24 hours. The water that separated was collected using a Dean-Stark trap. The mixture was then washed with 1.0 M sodium hydroxide solution (100 mL) and brine (100 mL). The organic phase was separated and concentrated under vacuum to give a brown, crude oil. The crude oil was filtered through a bed of neutral alumina and eluted with a mixture of ethyl acetate and hexane (1:5 by volume). The filtrate was concentrated to give a yellow oil (82.47 grams).

The oil from above (50.00 grams, 0.11 moles) was mixed with dichloromethane (500 mL) and cooled using an ice bath. 3-Chloroperbenzoic acid (58.30 grams, 0.24 mmoles, 70% in water) was added portion-wise over 5 minutes. The mixture was stirred for 2.5 days at room temperature and then filtered. The filtrate was diluted with ethyl acetate (500 mL), and then washed with 1.0 M sodium hydroxide solution (300 mL) and brine (200 mL). The organic phase was separated and concentrated under vacuum to give a colorless oil (50.99 grams).

Examples 3 to 15

An epoxy compound and a single curing agent curative as listed in Table 1 were thoroughly mixed together in a plastic cup. Bonds were prepared as described above on clean steel and cured for 16 hours at 150° C. (Examples 3 to 8) or for 2 hours at 180° C. (Examples 9 to 15). Overlap shear strengths of the cured adhesives are shown in Table 1.

TABLE 1

Examples 3 to 15

| Example | Epoxy compound | Epoxy Compound (grams) | Curing Agent | Curing Agent (grams) | OLS Strength (psi) |
|---|---|---|---|---|---|
| 3 | Example 1 | 1.00 | FA | 0.19 | 0 (fluid) |
| 4 | Example 1 | 1.00 | DFA | 0.22 | 1160 ± 184 |
| 5 | Example 1 | 1.00 | DFA II | 0.23 | 559 ± 231 |
| 6 | Example 1 | 1.00 | DTA | 0.54 | 154 ± 45 |
| 7 | Example 1 | 1.00 | TEKA | 0.54 | 0 (fluid) |
| 8 | Example 1 | 1.00 | K54 | 1.05 | 0 (fluid) |
| 9 | Example 2 | 1.50 | DHAA | 0.89 | 1221 ± 192 |
| 10 | Example 2 | 1.32 | DTA | 0.74 | 351 ± 41 |
| 11 | Example 2 | 1.31 | FA | 0.26 | 42 ± 4 |
| 12 | Example 2 | 1.31 | DFA | 0.30 | 3373 ± 220 |
| 13 | Example 2 | 1.31 | DFA II | 0.32 | 1674 ± 263 |
| 14 | Example 2 | 1.30 | K54 | 0.74 | 157 ± 33 |
| 15 | Example 2 | 1.32 | TEKA | 1.10 | 231 ± 27 |

Examples 16 to 17 and Comparative Example 1 (C1)

For Comparative Example 1, the epoxy compound ERISYS GE-60 was cured using ANCAMINE K54. For Examples 16, the epoxy compound of Example 1 was mixed with ERISYS GE-60 and cured using ANCAMINE K54. For Example 17, the epoxy compound of Example 1 was mixed with ERISYS GE-60 and cured with a combination of maleic anhydride and ANCAMINE K54. The amount of each component in the curable composition is shown in Table 2 along with the overlap shear strength for the resulting cured composition.

TABLE 2

Examples 16-17 and Comparative Example 1

| Example | ERISYS GE-60 (grams) | Ex 1 (grams) | Maleic Anhydride (grams) | K54 (grams) | OLS Strength (psi) |
|---|---|---|---|---|---|
| C1 | 1.00 | 0.00 | 0.00 | 1.36 | 265 ± 20 |
| 16 | 0.50 | 1.00 | 0.00 | 0.68 | 1127 ± 153 |
| 17 | 0.50 | 1.00 | 0.54 | 0.70 | 1540 ± 192 |

Examples 18 to 21

The epoxy compound of Example 1 was mixed with the epoxy compound D.E.R. 331. For Examples 18 and 20, the epoxy compound mixture was cured using IPDA. The IPDA was added and the resulting curable composition was mixed with a high speed mixer (DAC 400, which is commercially available from FlackTek, Inc. (Landrum, S.C., USA). For Examples 19 and 21, the epoxy mixture was combined with BPA in a glass vial and heated at 140° C. until the BPA was completely melted. The mixture was cooled to a liquid at room temperature and mixed well using the high speed mixer. IPDA was added and the resulting curable compositions were mixed further using the high speed mixer.

Each example was analyzed using DSC to determine the glass transition temperature as described above. The cure temperature was determined for Examples 18 and 19 as described above.

TABLE 3

Examples 18 to 21

| Example | Ex 1 (grams) | D.E.R. 331 (grams) | BPA (grams) | IPDA (grams) | Cure Temperature (° C.) | $T_g$ (° C.) |
|---|---|---|---|---|---|---|
| 18 | 1.00 | 0.14 | 0.00 | 0.20 | 154 | −18 |
| 19 | 1.02 | 0.15 | 0.27 | 0.20 | 126 | 26 |
| 20 | 1.00 | 1.50 | 0.00 | 0.53 | ND | 50 |
| 21 | 1.00 | 1.50 | 0.70 | 0.52 | ND | 52 |

ND means not determined

We claim:
1. A compound that is

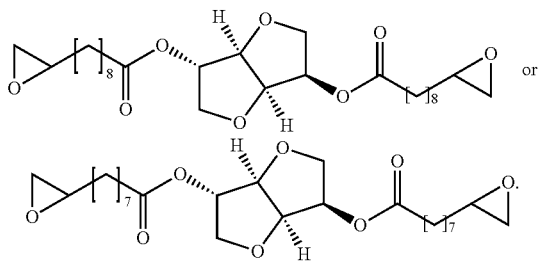

* * * * *

UNITED STATES PATENT AND TRADEMARK OFFICE
CERTIFICATE OF CORRECTION

| | |
|---|---|
| PATENT NO. | : 9,932,438 B2 |
| APPLICATION NO. | : 14/363862 |
| DATED | : April 3, 2018 |
| INVENTOR(S) | : Kwame Owusu-Adom |

It is certified that error appears in the above-identified patent and that said Letters Patent is hereby corrected as shown below:

In the Specification

Column 2
Line 38 (approx.), delete "groups" and insert -- groups. --, therefor.
Line 46, delete "groups" and insert -- groups. --, therefor.

Column 3
Line 52, delete "L-(CO)O—." and insert -- —L-(CO)O—. --, therefor.

Column 4
Line 46 (approx.), delete "stereroisomers." and insert -- stereoisomers. --, therefor.

Column 6
Lines 34-35, delete "sorbital" and insert -- sorbitol --, therefor.
Lines 38-39, delete "/equiveltn)," and insert -- /equivalent), --, therefor.

Column 7
Line 57, delete "dihydroxydiphenylpropylenphenylmethane," and insert
-- dihydroxydiphenylpropylphenylmethane, --, therefor.

Column 8
Line 1, delete "DER" and insert -- D.E.R. --, therefor.

Column 9
Line 48 (approx.), delete "difurlyamines" and insert -- difurylamines --, therefor.

Column 10
Line 23, delete "isophorene" and insert -- isophorone --, therefor.

Signed and Sealed this
Twenty-fifth Day of September, 2018

Andrei Iancu
*Director of the United States Patent and Trademark Office*

Column 19
Line 36 (approx.), delete "Alfar" and insert -- Alfa --, therefor.